United States Patent
Gorrepati

(10) Patent No.: US 9,486,454 B2
(45) Date of Patent: Nov. 8, 2016

(54) HYDRAZALINE HYDROCHLORIDE PELLETS AND METHOD OF PREPARATION

(71) Applicant: Navaneeta K. Gorrepati, DeSoto, TX (US)

(72) Inventor: Navaneeta K. Gorrepati, DeSoto, TX (US)

( * ) Notice: Subject to any disclaimer, the term of this patent is extended or adjusted under 35 U.S.C. 154(b) by 0 days.

(21) Appl. No.: 14/620,405

(22) Filed: Feb. 12, 2015

(65) Prior Publication Data

US 2015/0306097 A1    Oct. 29, 2015

(51) Int. Cl.
*A61K 31/502* (2006.01)
*A61K 9/50* (2006.01)

(52) U.S. Cl.
CPC .......... *A61K 31/502* (2013.01); *A61K 9/5015* (2013.01); *A61K 9/5026* (2013.01); *A61K 9/5042* (2013.01); *A61K 9/5047* (2013.01); *A61K 9/5078* (2013.01)

(58) Field of Classification Search
CPC ............. A61K 31/502; A61K 9/5015; A61K 9/5026; A61K 9/5042; A61K 9/5047; A61K 9/5078
See application file for complete search history.

(56) References Cited

U.S. PATENT DOCUMENTS

| | | | | |
|---|---|---|---|---|
| 5,445,829 A * | 8/1995 | Paradissis | ........... | A61K 9/5078 424/457 |
| 2007/0098791 A1 * | 5/2007 | Rekhi | ................ | A61K 9/5084 424/468 |
| 2009/0306081 A1 * | 12/2009 | Letts | .................... | A61K 9/2054 514/247 |
| 2010/0272793 A1 * | 10/2010 | Gorrepati | ........... | A61K 9/2009 424/456 |

OTHER PUBLICATIONS

Mughal et al. ("Coated hydralazine hydrochloride beads for sustained release after oral administration," Drug Development and Industrial Pharmacy, 2013; 39(9): 1439-1446).*

* cited by examiner

*Primary Examiner* — Aradhana Sasan

(57) ABSTRACT

Embodiments of a hydrazaline hydrochloride composition for treatment of hypertension in humans each provide sustained release of hydralazine hydrochloride administered in the form of pellets, granules and tablets. Methods of preparation are disclosed.

7 Claims, 9 Drawing Sheets

---

Hydralazine Hydrochoride SR (sustained release) pellets:

Example: 1

| Ingredients | Range in % | Function |
|---|---|---|
| Hydralazine Hydrochloride | 20% to 40% | Active drug content |
| Sugar spheres | 40% to 70% | Core |
| Sugar powder | 10% to 30% | Diluents |
| Hydroxy propyl methyl cellulose | 1.5% to 3.2 % | Binding Agent |
| Ethyl Cellulose (N 50) | 4.2% to 6.8% | Control Polymer |
| Stearic Acid | 0.22% to 0.53% | Film Forming Agent |
| Talc | 3.2% to 5.6% | Glidant |
| Isopropyl Alcohol | Quantity Sufficient | Solvent |

Hydralazine Hydrochoride SR (sustained release) pellets:

Example: 1

| Ingredients | Range in % | Function |
|---|---|---|
| Hydralazine Hydrochloride | 20% to 40% | Active drug content |
| Sugar spheres | 40% to 70% | Core |
| Sugar powder | 10% to 30% | Diluents |
| Hydroxy propyl methyl cellulose | 1.5% to 3.2 % | Binding Agent |
| Ethyl Cellulose (N 50) | 4.2% to 6.8% | Control Polymer |
| Stearic Acid | 0.22% to 0.53% | Film Forming Agent |
| Talc | 3.2% to 5.6% | Glidant |
| Isopropyl Alcohol | Quantity Sufficient | Solvent |

FIG. 5

Example: 2

| Ingredients | Range in % | Function |
|---|---|---|
| Hydralazine Hydrochloride | 20% to 40% | Active drug content |
| Microcrystalline cellulose | 40% to 70% | Core |
| Sugar powder | 10% to 30% | Diluents |
| Polyvinyl pyrrolidine K 30 | 1.5% to 3.2 % | Binding Agent |
| Eudragit Polymer | 4.2% to 6.8% | Control Polymer |
| Stearic Acid | 0.22% to 0.53% | Film Forming Agent |
| Talc | 3.2% to 5.6% | Glidant |
| Isopropyl Alcohol | Quantity Sufficient | Solvent |

FIG. 6

Example: 3

| Ingredients | Range in % | Function |
|---|---|---|
| Hydralazine Hydrochloride | 20% to 40% | Active drug content |
| Starch core | 40% to 70% | Core |
| Sugar powder | 10% to 30% | Diluents |
| Polyvinyl pyrrolidine K 30 | 1.5% to 3.2 % | Binding Agent |
| Guar gum/xanthane gum | 4.2% to 6.8% | Control Polymer |
| Stearic Acid | 0.22% to 0.53% | Film Forming Agent |
| Talc | 3.2% to 5.6% | Glidant |
| Purified water | Quantity Sufficient | Solvent |

FIG. 7

Example: 4

| Ingredients | Range in % | Function |
|---|---|---|
| Hydralazine Hydrochloride | 20% to 40% | Active drug content |
| Sugar core | 40% to 70% | Core |
| Sugar powder | 10% to 30% | Diluents |
| Starch paste | 1.5% to 3.2 % | Binding Agent |
| Guar gum/xanthane gum | 4.2% to 6.8% | Control Polymer |
| Stearic Acid | 0.22% to 0.53% | Film Forming Agent |
| Talc | 3.2% to 5.6% | Glidant |
| Purified water | Quantity Sufficient | Solvent |

FIG. 8

Example: 5

| Ingredients | Range in % | Function |
|---|---|---|
| Hydralazine Hydrochloride | 20% to 40% | Active drug content |
| Sugar spheres | 40% to 70% | Core |
| Sugar powder | 10% to 30% | Diluents |
| Hydroxy propyl methyl cellulose | 1.5% to 3.2 % | Binding Agent |
| Hydroxy Propyl cellulose | 4.2% to 6.8% | Control Polymer |
| Stearic Acid | 0.22% to 0.53% | Film Forming Agent |
| Talc | 3.2% to 5.6% | Glidant |
| Isopropyl Alcohol | Quantity Sufficient | Solvent |

FIG. 9

Example: 6

| Ingredients | Range in % | Function |
|---|---|---|
| Hydralazine Hydrochloride | 20% to 40% | Active drug content |
| Mannitol | 16% to 25% | Osmotic agent |
| Polyvinyl pyrrolidine K 30 | 8% to 10% | Binding Agent |
| Lactose monohydrate | 35% to 60% | Diluent |
| Microcrystalline cellulose | 18% to 25% | Disintegrant |
| Magnesium stearate | 3% to 8% | Lubricant |
| Purified water | Quantity Sufficient | Solvent |
| Coating Solution (Up to 100 ml) (Total solids in coating 4%) | | |
| Cellulose Acetate | 3gms | |
| Sorbitol | 0.2% to 0.4% | |
| Dibutyl Phthalate | 15% | |
| Acetone : Purified water | Up to 100ml | |

FIG. 10

Example: 7

| Ingredients | Range in % | Function |
|---|---|---|
| Hydralazine Hydrochloride | 20% to 40% | Active drug content |
| Mannitol | 15% to 25% | Osmotic agent |
| Hydroxy propyl methyl cellulose/ or Starch paste | 10% to 15% | Binding Agent |
| Lactose monohydrate | 40% to 62% | Diluent |
| Microcrystalline cellulose | 20% to 30% | Disintegrant |
| Magnesium stearate | 5% to 8% | Lubricant |
| Purified water | Quantity Sufficient | Solvent |
| Coating Solution (Up to 100 ml) (Total solids in coating 4%) | | |
| Cellulose Acetate | 3gms | |
| Sorbitol | 5% to 10% | |
| Dibutyl Phthalate | 15% | |
| Acetone : Purified water | Up to 100ml | |

FIG. 11

Example: 8

| Ingredients | Range in % | Function |
|---|---|---|
| Hydralazine Hydrochloride | 20% to 40% | Active drug content |
| Sodium chloride | 15% to 45% | Osmotic agent |
| Microcrystalline cellulose | 10% to 15% | Diluent |
| Guar gum | 4% to 15% | Glident |
| Providone K 30 | 6% | Binding Agent |
| Sodium lauryl suphate | 4% | Surfactant |
| Magnesium stearate | 1% | Lubricant |
| Coating Solution (Up to 100 ml) (Total solids in coating 4%) | | |
| Eudragit L 100-55 | 3gms | |
| PEG 400 | 5% to 10% | |
| Dibutyl Phthalate | 15% | |
| Glycerine | Up to 100ml | |

FIG. 12

Example: 9

| Ingredients | Range in % | Function |
|---|---|---|
| Hydralazine Hydrochloride | 20% to 40% | Active drug content |
| Lactose monohydrate | 20% to 38% | Diluent |
| Sodium Chloride | 10% to 12.5% | Osmotic agent |
| Hypromellose K4M | 25% | Hydrophillic polymer |
| Magnesium stearate | 1% to 2% | Lubricant |
| Coating Solution (Up to 100 ml) (Total solids in coating 4%) | | |
| Cellulose Acetate | 7% | |
| PEG 400 | 1% | |
| PVP | 2.6% | |

FIG. 13

Example: 10

| Ingredients | Range in % | Function |
|---|---|---|
| Hydralazine Hydrochloride | 20% to 40% | Active drug content |
| Lactulose | 8% to 15% | Poly saccharide |
| Cross carmellose sodium | 8% to 10% | Disintegrant |
| Talc | 2% to 3% | Lubricant |
| Pactin | 25% to 40% | Poly saccharide |
| Guargum | 10% to 25% | Binding Agent |
| Hydroxy propyl methyl cellulose | 3% to 8% | Hydrophillic polymer |
| Hydroxy ethyl cellulose | 5% to 8% | Retard polymer |
| Eudragt S 100 | 10% to 12% | Enteric coated polymer |
| Cellulose acetate phthalate | 5% | Plasticizer |

FIG. 14

Example: 11

| Ingredients | Range in % | Function |
|---|---|---|
| Hydralazine Hydrochloride | 20% to 40% | Active drug content |
| Pectin | 20% to 35% | Poly saccharide |
| Sodium starch glycolate | 8% to 10% | Disintegrant |
| Talc | 2% to 3% | Lubricant |
| Eudragit RS | 5% to 8% | Polymer |
| PEG 6000 | 10% to 25% | Wetting agent |
| Hydroxy propyl methyl cellulose | 3% to 8% | Hydrophillic polumer |
| Hydroxy ethyl cellulose | 5% to 15% | Retard polymer |
| Eudragt S 100 | 10% to 15% | Enteric coated polymer |
| Cellulose acetate phthalate | 6% | Plasticizer |

FIG. 15

Example: 12

| Ingredients | Range in % | Function |
|---|---|---|
| Hydralazine Hydrochloride | 20% to 40% | Active drug content |
| Sugar Sphere (#60 to #80) | 35% to 55% | Core sucrose |
| Povidone K 30 | 10% to 12.5% | Binding agent |
| Hydroxypropyl methylcellulose E5 | 5% | Hydrophillic polymer |
| Eudragit L30D | 8% | Enteric coated polymer |
| PEG 6000 | 2% | Wetting agent |
| Titanium dioxide | 1% | Colouring agent |
| Talc | 1% | Glident |
| Purified water/ isopropyl alcohol | Quantity sufficient | Solvent |

FIG. 16

Example: 13

| Ingredients | Range in % | Function |
|---|---|---|
| Hydralazine Hydrochloride | 20% to 40% | Active drug content |
| Sugar Sphere (#60 to #80) | 35% to 55% | Core sucrose |
| Povidone K 30 | 10% to 12.5% | Binding agent |
| Hydroxy propyl methyl cellulose | 5% | Hydrophillic polymer |
| Eudragit RS 100 | 8% | Enteric coated polymer |
| PEG 6000 | 2% | Wetting agent |
| Titanium dioxide | 1% | Colouring agent |
| Talc | 1% | Glident |
| Purified water/ isopropyl alcohol | Quantity sufficient | Solvent |

FIG. 17

Example: 14

| Ingredients | Range in % | Function |
|---|---|---|
| Hydralazine Hydrochloride | 20% to 40% | Active drug content |
| Sugar Sphere (#60 to #80) | 35% to 55% | Core sucrose |
| Sugar syrup | 10% to 12.5% | Binding agent |
| Hydroxypropyl methyl-cellulose E5 | 5% | Hydrophillic polymer |
| Eudragit L30D | 8% | Enteric coated polymer |
| PEG 6000 | 2% | Wetting agent |
| Titanium dioxide | 1% | Colouring agent |
| Talc | 1% | Glident |
| Purified water/ isopropyl alcohol | Quantity sufficient | Solvent |

FIG. 18

HYDRAZALINE HYDROCHLORIDE PELLETS AND METHOD OF PREPARATION

BACKGROUND OF THE DISCLOSURE

Field of the Disclosure

The disclosure relates to a method of preparing a controlled release pharmaceutical formulation of hydralazine hydrochloride pellets which are used in the treatment of hypertension in humans.

SUMMARY OF THE DISCLOSURE

An embodiment of the disclosure meets the needs presented above by generally comprising a sustained release hydralazine hydrochloride composition in the form of pellets, granules and tablets.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF THE DRAWINGS

The disclosure will be better understood and objects other than those set forth above will become apparent when consideration is given to the following detailed description thereof. Such description makes reference to the annexed drawings wherein:

Stability studies were performed above the formulations accelerated conditions at 40 degrees Celsius/75% relative humidity 1, 2, 3, and 6 months and real time conditions at 25 degrees Celsius/65% relative humidity at 0, 3, 6, 9, 12, 18, 24, 30, and 36 months. Analysed data each time point drug release, potency and physical appearance. All parameters are found within specified limits. Average drug release profile from various formulations are given in the below figures.

FIG. 5 is a chart of a sustained release pellet formulation according to an embodiment of the disclosure.

FIG. 6 is a chart of a second sustained release pellet formulation according to an embodiment of the disclosure.

FIG. 7 is a chart of a third sustained release pellet formulation according to an embodiment of the disclosure.

FIG. 8 is a chart of a fourth sustained release pellet formulation according to an embodiment of the disclosure.

FIG. 9 is a chart of a fifth sustained release pellet formulation according to an embodiment of the disclosure.

FIG. 10 is a chart of a sustained release osmotic tablet formulation according to an embodiment of the disclosure.

FIG. 11 is a chart of a second sustained release osmotic tablet formulation according to an embodiment of the disclosure.

FIG. 12 is a chart of a third sustained release osmotic tablet formulation according to an embodiment of the disclosure.

FIG. 13 is a chart of a fourth sustained release osmotic tablet formulation according to an embodiment of the disclosure.

FIG. 14 is a chart of a sustained release tablet formulation by multi-layered coating technology according to an embodiment of the disclosure.

FIG. 15 is a chart of a second sustained release tablet formulation by multi-layered coating technology according to an embodiment of the disclosure.

FIG. 16 is a chart of a sustained release pellet formulation by multiple unit pellet system technology according to an embodiment of the disclosure.

FIG. 17 is a chart of a second sustained release pellet formulation by multiple unit pellet system technology according to an embodiment of the disclosure.

FIG. 18 is a chart of a third sustained release pellet formulation by multiple unit pellet system technology according to an embodiment of the disclosure.

DESCRIPTION OF THE PREFERRED EMBODIMENT

Figure 1:
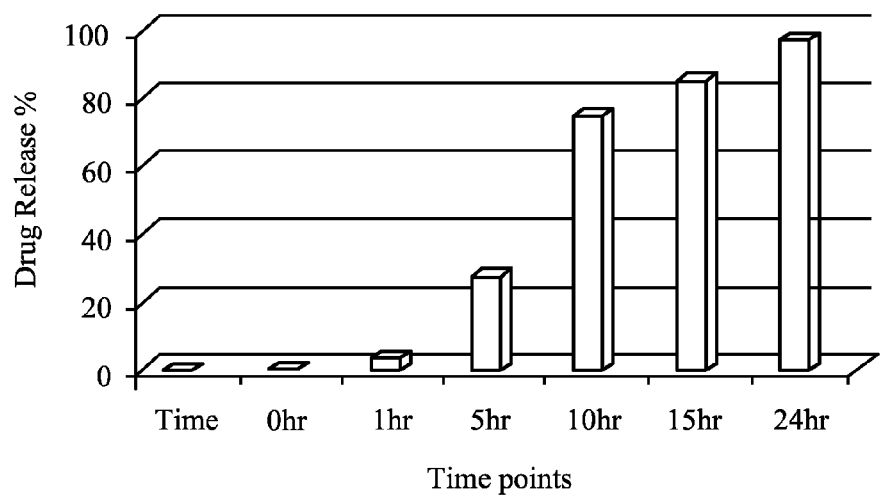
FIG. 1 shows the drug release profile of hydralazine hydrochloride sustained release pellets.
Figure 2:
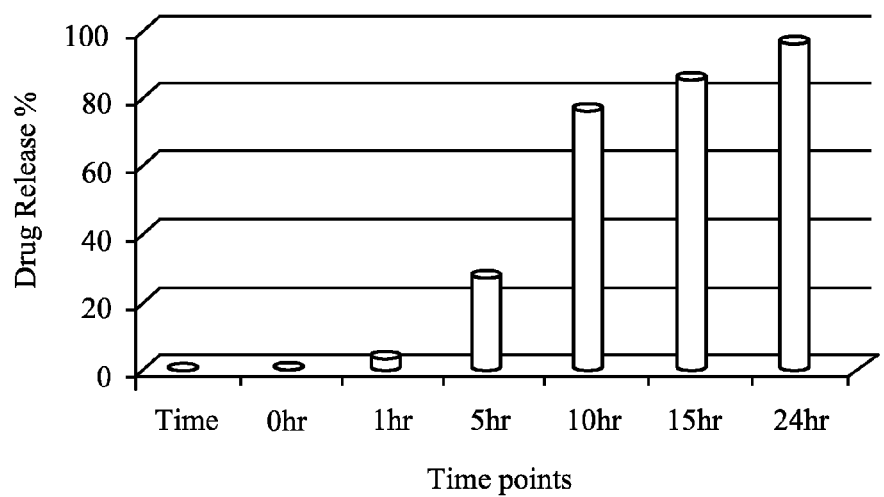
FIG. 2 shows the drug release profile of hydralazine hydrochloride osmotic tablets.
Figure 3:
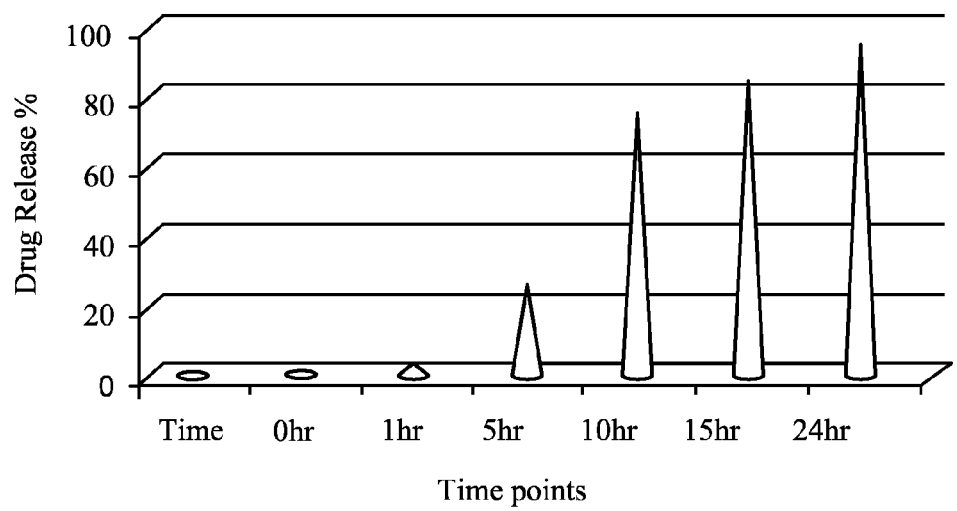
FIG. 3 shows the drug release profile of hydralazine hydrochloride sustained release tablets by multi-layered coating technology.
Figure 4:
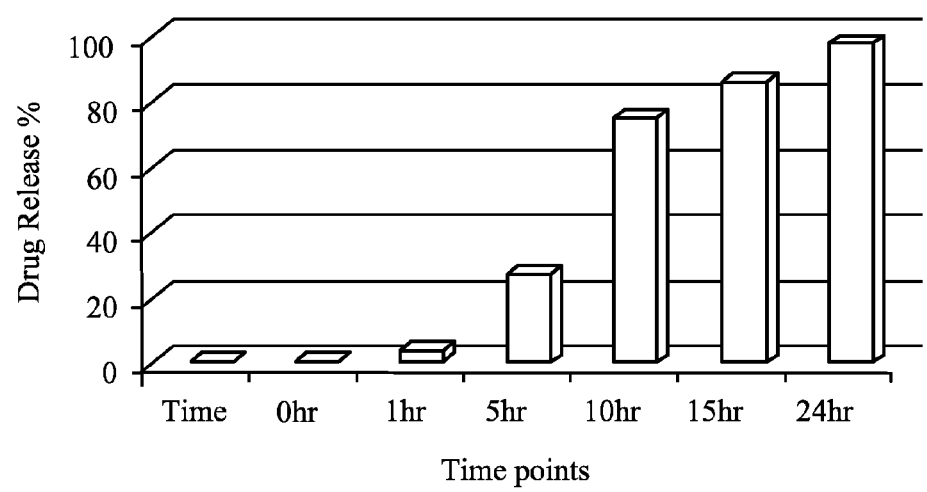
FIG. 4 shows the drug release profile of hydralazine hydrochloride MUPS pellets in tablet form.

With reference now to the drawings, and in particular to FIGS. 1 through 6 thereof, a new hydralazine hydrochloride pharmaceutical composition embodying the principles and concepts of an embodiment of the disclosure and will be described.

The present invention is further illustrated by the examples provided in the charts within the drawing FIGS. 5 through 9, 10 through 13, 14 through 15, and 16 through 18.

The composition is provided with a core of sugar spheres each having a size between 750 microns and 810 microns layered with a drug layer containing hydrazaline hydrochloride, a separating layer, an enteric layer comprising an enteric polymer and then a top layer. The end product can be administered over a span of 12-24 hours.

In the sample formulations shown in FIGS. 5 through 9, a process of making the hydrazaline hydrochloride composition begins with drug layering by preparation of a first coating solution of a slurry of hydralazine hydrochloride in a solution of hydroxy propyl methyl cellulose in isopropyl alcohol or a solution of polyvinyl pyrrolidine K 30 in isopropyl alcohol or a solution of polyvinyl pyrrolidine K 30 in purified water or a solution of starch in purified water. Sugar spheres of 750-810 microns in size form a core. Depending on the particular formulation the sugar spheres or microcrystalline cellulose spheres or starch spheres are preheated to about 35 degrees Celsius with gentle movement in a fluid bed coater and then sprayed with the first coating solution prepared above, while more air drying is introduced and fluidization intensified. Spray rate, air throughput and inlet air temperature are adjusted in such a way that the core bed reaches a temperature about 35 degrees Celsius. Over wetting of the cores is to be avoided as it may cause conglomeration. The pellets formed are then dried in a tray drier at about 45 degrees Celsius to a moisture content of less than three percent. The dried pellets are sized on a sifter to remove agglomerates, broken pellets, and fine powder. The pellets are then ready for coating.

A second solution of ethyl cellulose, stearic acid and hydroxy propyl methyl cellulose is prepared in an adequate quantity of isopropyl alcohol. Alernatively, the second coating solution is eudragit and stearic acid is prepared in an adequate quantity of isopropyl alcohol. Yet another alternative second coating solution is guar gum/xanthane gum and stearic acid prepared in an adequate quantity of purified water. The drug pellets are preheated to about 35 degrees Celsius with gentle movement in a fluid bed coater, and then sprayed with the second coating solution, while more drying air is introduced and fluidization intensified. Spray rate, air throughput and inlet air temperature are adjusted in such a way that the core bed reaches a temperature of about 35 degrees Celsius. Over wetting is to be avoided as it may cause agglomeration. After a complete of the second coating solution is consumed, the fluidization is reduced for a brief post-drying period. The resulting pellets are then dried in a tray drier at about 45 degrees Celsius to a moisture content of less than three percent. The resulting pellets are sized on a sifter to remove agglomerates, broken pellets and fine powder. After checking weight of the resulting pellets and noting down the yield they are ready to fill in capsules.

In variations of the invention represented in FIGS. 10 through 13, the composition of hydrazaline hydrochloride is made using the following process. Hydrazaline hydrochloride is mixed with manitol, povidone K-30, lactose and microcrystalline cellulose then passed through 30 mesh screen producing a blend. The blend is mixed for between 8 and 12 minutes and granulated with starch paste. The resulting wet mass is passed through a #18 sieve to produce granules. The granules are dried at 60 degrees Celsius in a hot air oven for between 25 and 30 minutes after which the granules are passed through a #22 sieve. The sized granules are then blended with magnesium stearate for between 8 and 12 minutes and compressed into tablets.

The tablets are coated with ten percent sorbitol. Various components of the coating solution are added to the solvent in a sequential manner. Each component added is allowed to dissolve prior to adding the next component. To coat, the tablets are placed in a coating pan. The pan is rotated between 15 and 18 revolutions per minute. The coating is performed using a spray gun at a spray rate of three to five ml per minute. The atomization pressure is kept at 1 kg per square cm while outlet temperature was kept between 40 and 45 degrees Celsius. Coating is continued until a desired weight gain of between 9 and 11 percent.

In variations of the invention represented in FIGS. 14 and 15, the composition of hydrazaline hydrochloride is made using the following process. Hydrazaline hydrochloride core tablets are prepared by polysaccharide (lactulose), disintegrant and lubricant by a conventional direct compression method. The core tablets are coated with pH 5.6 depended polymer followed by enteric polymer at a pH above 7.0. The top layer contains a eudragit polymer pH above 7.0 which will not break or dissolve at the stomach but pass to the duodenum, jejunum and ileum followed by the large intestine.

In variations of the invention represented by exemplary formulations in FIGS. 16 through 18, the composition of hydrazaline hydrochloride is made using the following process. A slurry of hydrazaline hydrochloride is prepared in a solution of hydroxy propyl methyl cellulose in isopropyl alcohol or a solution of polyvinyl pyrrolidine K 30 in isopropyl alcohol. Sugar spheres (size 60#80) are preheated to about 35 degrees Celsius with gentle movement in a fluid bed coater and then sprayed with one of the coating solutions as disclosed above, while more drying air is introduced and fluidization intensified. Dried pellets produced are sized with mesh #40 and #50 to provide micro pellets. The micro pellets are coated with hydroxy propyl methyl cellulose as a barrier coating and followed by an enteric coating of a solution of eudragit and PEG 6000 in an adequate quantity of either purified water or isopropyl alcohol. The coated micro pellets are then ready to be formed into tablets prepared by a multiple unit pellet system along with diluent, disintegrant, and lubricants in a conventional manner followed by film coating.

In use, each preparation provides a sustained release of a therapeutic dose of hydrazaline hydrochloride for treatment of hypertension in humans.

Therefore, the foregoing is considered as illustrative only of the principles of the disclosure. Further, since numerous modifications and changes will readily occur to those skilled in the art, it is not desired to limit the disclosure to the exact construction and preparation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A sustained release pharmaceutical composition of hydralazine hydrochloride comprising:
   20-40% by total weight of active drug content of hydralazine hydrochloride;
   40-70% by total weight of a core, wherein the core is one of a sugar sphere, a microcrystalline cellulose and a starch;
   10-30% by total weight of diluent;
   1.5-3.2% by total weight of binding agent;
   4.2-6.8% by total weight of control polymer, wherein the control polymer is one of ethyl cellulose, acrylic polymer, guar gum, xanthane gum, and hydroxypropyl cellulose;
   0.22-0.53% by total weight of film forming agent;
   3.2-5.6% by total weight of glidant; and
   a solvent.

2. The composition of claim 1, wherein the diluent is sugar powder.

3. The composition of claim 1, wherein the binding agent is one of hydroxy propyl methyl cellulose and polyvinyl pyrrolidine.

4. The composition of claim 1, wherein the film forming agent is stearic acid.

5. The composition of claim 1, wherein the glidant is talc.

6. The composition of claim 1, wherein the solvent is one of isopropyl alcohol and purified water.

7. The composition of claim 1, wherein said composition is in a form selected from a group of forms consisting of pellets, granules, and tablets.

* * * * *